(12) United States Patent
Burren et al.

(10) Patent No.: US 8,721,601 B2
(45) Date of Patent: May 13, 2014

(54) DOSE SETTING MECHANISM FOR AN INJECTION DEVICE

(75) Inventors: Stefan Burren, Bremgarten (CH); Ulrich Moser, Heimiswil (CH); Christian Schrul, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 706 days.

(21) Appl. No.: 11/943,818

(22) Filed: Nov. 21, 2007

(65) Prior Publication Data

US 2008/0183139 A1    Jul. 31, 2008

Related U.S. Application Data

(63) Continuation of application No. PCT/CH2006/000237, filed on Apr. 28, 2006.

(30) Foreign Application Priority Data

May 24, 2005 (DE) .......................... 10 2005 023 824

(51) Int. Cl.
*A61M 5/00* (2006.01)

(52) U.S. Cl.
USPC .......................................... 604/211; 604/207

(58) Field of Classification Search
USPC .................. 604/110, 181, 187, 500, 207–211
See application file for complete search history.

(56) References Cited

U.S. PATENT DOCUMENTS

| | | | |
|---|---|---|---|
| 3,128,765 A | 4/1964 | Howard | |
| 4,583,978 A | 4/1986 | Porat et al. | |
| 5,114,406 A * | 5/1992 | Gabriel et al. | 604/136 |
| 5,308,340 A | 5/1994 | Harris et al. | |
| 6,086,567 A * | 7/2000 | Kirchhofer et al. | 604/211 |
| 6,193,698 B1 * | 2/2001 | Kirchhofer et al. | 604/211 |
| 2004/0019333 A1 * | 1/2004 | Graf et al. | 604/207 |
| 2004/0260247 A1 * | 12/2004 | Veasey et al. | 604/207 |
| 2005/0177115 A1 * | 8/2005 | Broennimann et al. | 604/208 |
| 2012/0157932 A1 * | 6/2012 | Glejbol et al. | 604/211 |

FOREIGN PATENT DOCUMENTS

| | | |
|---|---|---|
| DE | 202 09 051 U1 | 5/2003 |
| DE | 10 2005 001 159 | 7/2006 |
| EP | 0 828 527 | 3/1998 |
| EP | 0 937 471 A | 8/1999 |
| WO | WO 97/36626 | 10/1997 |
| WO | WO 2004/007001 | 1/2004 |
| WO | WO 2004/078239 | 9/2004 |

* cited by examiner

*Primary Examiner* — Kami A Bosworth
*Assistant Examiner* — Imani Hayman
(74) *Attorney, Agent, or Firm* — Dorsey & Whitney LLP; Stuart R. Hemphill, Esq.

(57) ABSTRACT

A dosing device for setting a dose to be delivered by an injection device, the dosing device including a setting element, e.g. a setting sleeve, and a drawing element, e.g. a rotating sleeve, which can be rotated out of the dosing device for preparing a dose delivery. A stop is on the setting element, and a counter stop is on the drawing element so that a rotational motion of the drawing element relative the setting element can be limited by the stops. The present invention encompasses a method for setting a dose that should be delivered by an injection device, wherein the dose to be delivered can be set by a setting element, e.g. a setting sleeve, and a drawing element of the injection device, e.g. a rotating sleeve, can subsequently draw up the dose by effecting a rotational motion to deliver the set dose from the injection device in a subsequent step. According to the present invention, the setting process is isolated from drawing process.

20 Claims, 8 Drawing Sheets

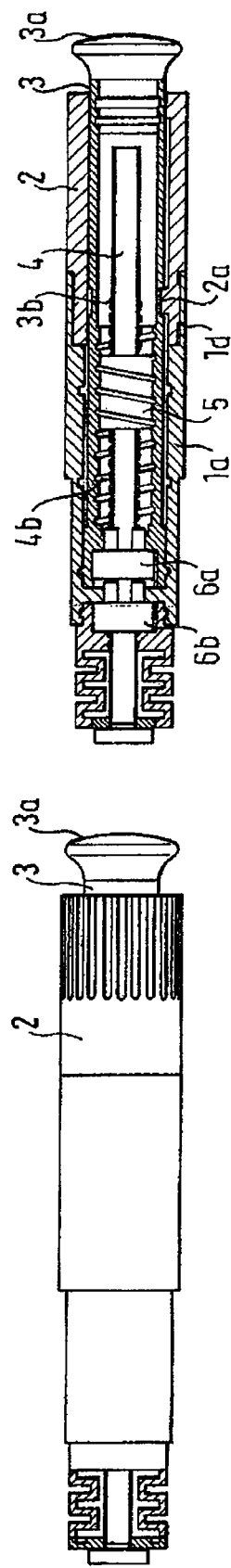
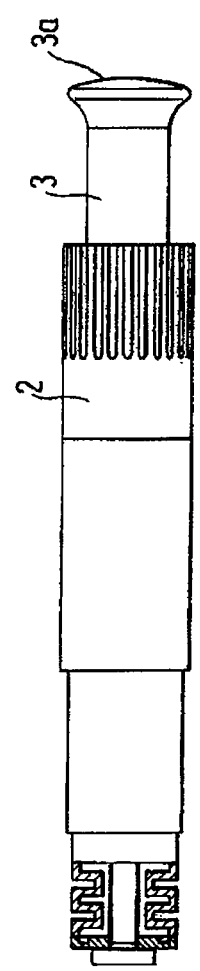
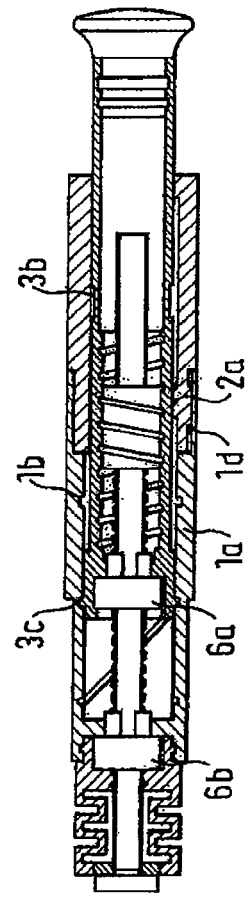
FIG. 2A
FIG. 2B

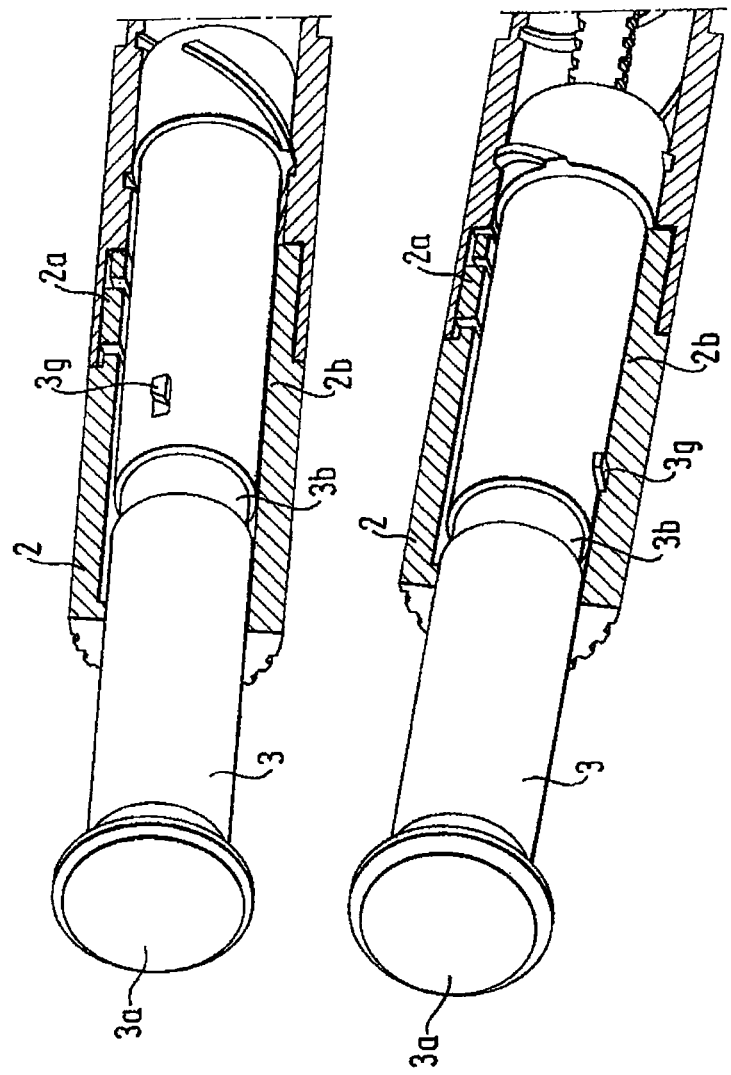

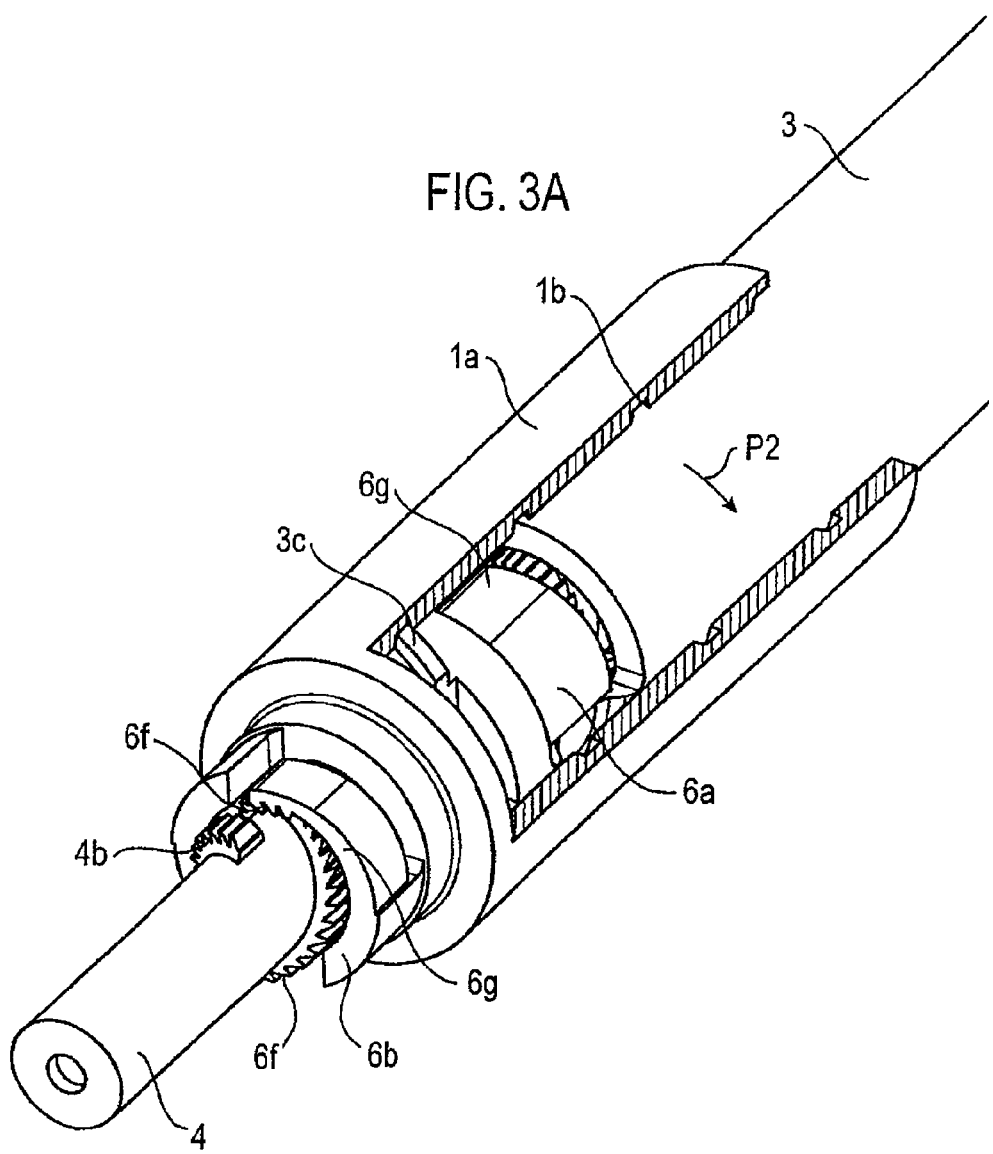

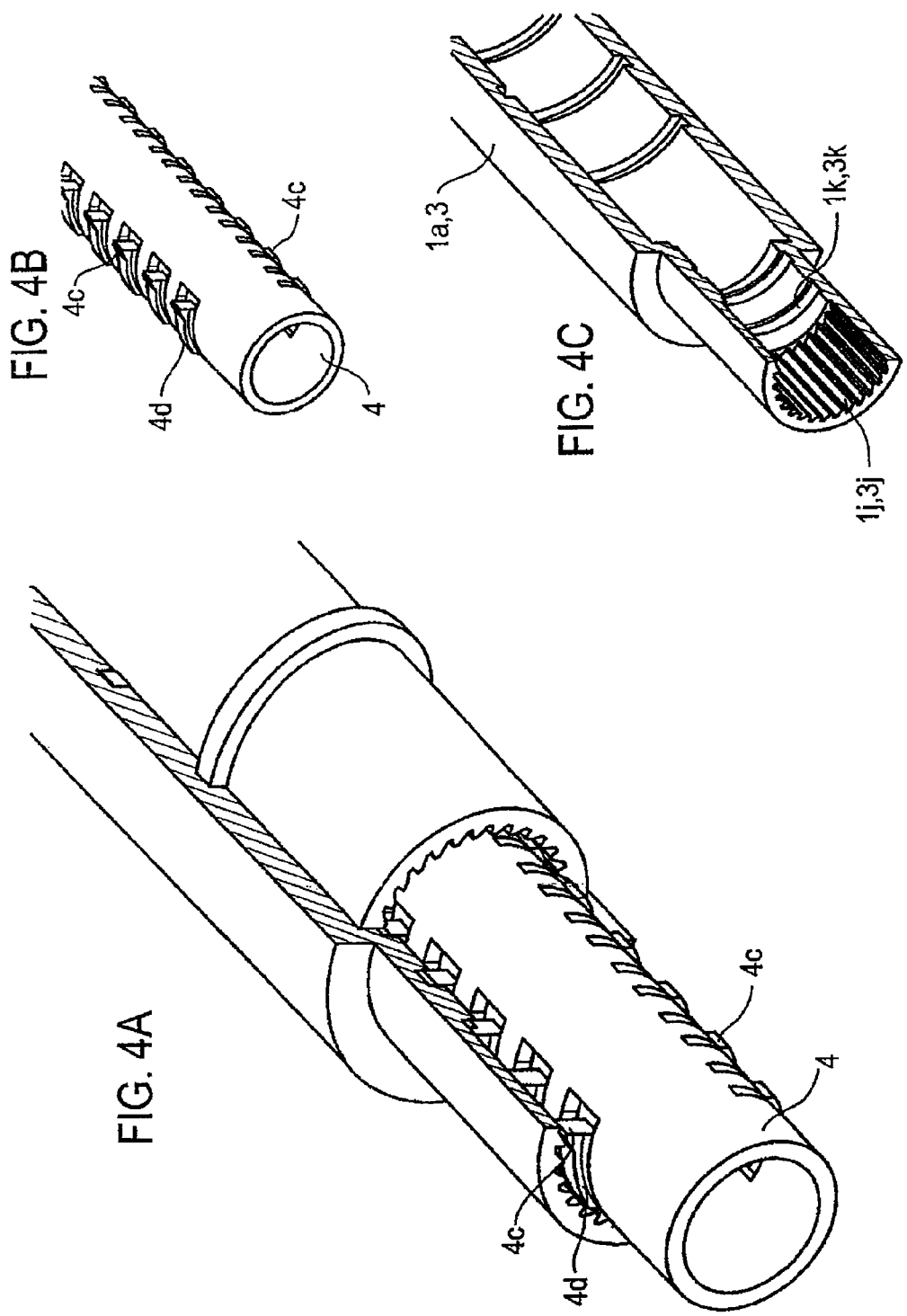

DOSE SETTING MECHANISM FOR AN INJECTION DEVICE

CROSS-REFERENCE TO RELATED APPLICATIONS

This application is a continuation of International Application No. PCT/CH2006/000237 filed on Apr. 28, 2006, which claims priority to German Application No. DE 10 2005 023 824.6 filed on May 24, 2005, the contents of both of which are incorporated in their entirety herein by reference.

BACKGROUND

The present invention relates to devices for dispensing, injecting, administering, delivering or infusing substances, and to methods of making and using such devices. More particularly, it relates to a dose setting mechanism for an injection device by which a dose or quantity of a substance to be dispensed from or with the aid of an injection device can be set or selected.

Document DE 202 09 051 U1 discloses an injection device with a dose setting element which is locked in an end position. The injection device has a dose setting element able to effect a rotating movement relative to the housing of the device from a first direction of rotation as far as an end position and in an opposite direction of rotation to select a dose. The dose setting element is coupled with a conveying mechanism by which a selected dose can be dispensed from a reservoir of the injection device. An anti-rotation lock prevents the dose setting mechanism from effecting a rotating movement in the first direction of rotation beyond an end position.

Patent specification EP 0 828 527 B1 discloses an injection device with a forward feed sleeve which is able to slide forward longitudinally, wherein a printed dose indicator enables a reading to be taken of the dose to be injected. A mechanism is provided which prevents the injection device from being charged when a push rod is pulled out if the supply of an ampoule has been fully used.

German patent application No. 10 2005 001 159.4 discloses a dose setting mechanism for an injection device with a ratio transmitting system by which a dose quantity, a small quantity in particular, can be exactly set and dispensed.

Patent specification WO 2004/078239 A1 discloses a device for administering medicaments, comprising a housing with an internal thread, a dose selection sleeve with a thread which locates in the internal thread of the housing, a rotating sleeve which is releasably connected to the dose selection sleeve and a coupling disposed between the dose selection sleeve and the rotating sleeve. The two sleeves are able to rotate relative to the housing when the dose selection sleeve and the rotating sleeve are coupled. When the dose selection sleeve and the rotating sleeve are uncoupled, the dose selection sleeve is able to rotate relative to the housing whereas the rotating sleeve is locked to prevent it from rotating relative to the housing, thereby enabling an axial movement of the rotating sleeve so that a force is transmitted in the longitudinal direction toward the proximal end of the device to administer medicaments.

SUMMARY

An object of the present invention is to provide a threaded rod and dose setting mechanism for setting and/or dispensing a dose to be dispensed from an injection device, to provide an injection device incorporating such a dose setting mechanism, as well as to provide a method by which a dose can be reliably set whereby the risk of incorrect operation when setting and/or dispensing the dose is reduced.

In one embodiment, the present invention comprises a dosing device for setting a dose to be delivered by an injection device, the dosing device comprising a setting element, e.g. a setting sleeve, and a drawing element, e.g. a rotating sleeve, which can be rotated out of the dosing device for preparing for dose delivery. A stop is on the setting element, and a counter stop is on the drawing element so that a rotational motion of the drawing element relative the setting element can be limited by the stops. The present invention encompasses a method for setting a dose that should be delivered by an injection device, wherein the dose to be delivered can be set by a setting element, e.g. a setting sleeve, and a drawing element of the injection device, e.g. a rotating sleeve, can subsequently draw up the dose by effecting a rotational motion to deliver the set dose from the injection device in a subsequent step. According to the present invention, the setting process is isolated from drawing process.

In one embodiment, the present invention comprises an injection device comprising a dose setting mechanism comprising a setting element and a priming element which can be turned out of the dose setting mechanism to prepare for dispensing a dose, the setting element and priming element each comprising a stop, the stops co-operating so that a rotating movement of the priming element relative to the setting element is restricted by the stops. In some embodiments, the setting element comprises a setting sleeve and the priming comprises a rotating sleeve, the priming element travels an axial priming path having a length, wherein the dose to be dispensed is proportional to the axial priming path length or the setting element is lockable relative to the injection device by a radially biased retaining element.

In one embodiment, the present invention comprises a method of setting a dose to be dispensed from an injection device comprising the steps of setting the dose to be dispensed by using a setting element, priming the injection device by using a priming element, and dispensing the set dose from the injection device, the setting step being independent from the priming step.

In one embodiment, the present invention relates to a dosing device for setting a dose to be delivered by an injection device, comprising a setting element, particularly a setting sleeve, and a drawing element, particularly a rotating sleeve, which can be rotated out of the dosing device for preparing a dose delivery. A stop is placed on the setting element, and a counter stop is placed on the drawing element so that a rotational motion of the drawing element relative the setting element can be limited by the stops. The invention also relates to a method for setting a dose that should be delivered by an injection device, whereby the dose to be delivered can be set by a setting element, particularly by a setting sleeve, and the injection device having a drawing element, particularly a rotating sleeve, can subsequently draw up the dose by effecting a rotational motion in order to deliver the set dose from the injection device in a subsequent step.

In one embodiment, the present invention comprises a dose setting mechanism for setting a dose to be dispensed from an injection device, comprising a setting element and a priming element which can be turned out of the dose setting mechanism to prepare for dispensing a dose, the setting element and priming element each comprising a stop, the stops co-operating so that a rotating movement of the priming element relative to the setting element is restricted by the stops. In some embodiments, the setting element comprises a setting sleeve and the priming comprises a rotating sleeve, the priming element travels an axial priming path having a length and the dose to be dispensed is proportional to the axial priming path length, and/or the setting element and the priming element are disposed coaxially and can be turned relative to one another.

By virtue of one aspect of the present invention, it relates to a dose setting mechanism for setting a dose of a medical substance, such as insulin or hormones, to be dispensed from an injection device, which is contained in the injection device or in an ampoule. The dose setting mechanism may be disposed on the injection device or may be provided as part of it, and has a setting sleeve at the rear end of the injection device which is rotatable about the longitudinal axis of the device and has one or more markings in a circumferential direction which indicate the quantity of a substance which can be dispensed from the injection device in the respective setting position or the quantity of the active ingredient contained in the substance which can be dispensed with a dose of the substance.

In some embodiments, by rotating the setting sleeve and a marking provided on the setting sleeve as far as a pre-defined point shown by an arrow on the injection device, a user can set the quantity of substance or active ingredient to be dispensed from the injection device in a subsequent dispensing operation. The dose setting mechanism also has a rotating sleeve, which can be rotated out of the dose setting mechanism or injection device, e.g., relative to a housing of the injection device or relative to the setting sleeve, to prepare for dispensing a dose. One or more markings are provided on the rotating sleeve and run or extend around the external face of it in the circumferential direction. These markings are, in terms of values, identical to the markings applied to the setting sleeve or can be associated with them.

In some embodiments, the rotating sleeve is coupled with the setting sleeve, e.g. directly via a thread engagement or indirectly by an intermediate element, so that when the rotating sleeve is in the state extracted fully or to the maximum which occurs with the maximum extraction or outward movement of the rotating sleeve from the setting or rotation position of the setting sleeve, it is positioned relative to the setting sleeve in such a way that a marking provided on the rotating sleeve is not offset from the associated marking of the setting sleeve in the circumferential direction, in other words lies in an axial extension of the marking on the rotating sleeve, so that dose blocks of a dose display on the rotating sleeve in the fully extracted state lie axially aligned with the corresponding dose display or marking of the setting sleeve with every dose setting operation effected by the setting sleeve. Thus, the dose can be set on one side of the pen and a check can easily be made at the same time on the same side of the pen to ensure that the dose has been primed correctly, due to the fact that the associated markings on the setting sleeve and the rotating sleeve lie adjacent to one another. If this is not the case, a user can easily tell that the set dose has not been primed and can therefore not be administered.

The setting sleeve can be coupled with the rotating sleeve by a threaded or other suitable engagement, in which case the rotating sleeve may be guided coaxially in the setting sleeve, which has an internal thread in which an external thread of the rotating sleeve engages. The setting sleeve and rotating sleeve may also be uncoupled, i.e. the setting sleeve may be rotatably mounted on the injection device to which the rotating sleeve is connected in a threaded engagement. In this respect, a stop element such as a raised area, web, stop or a stop bar, may be provided on the setting sleeve, which is disposed in the axial direction, in other words more or less parallel with the mid-axis of the injection device, to permit a 360° rotation of the rotating sleeve or extending circumferentially on the internal face of the setting sleeve, e.g. in the form of a thread or threaded portion, to permit a rotation of the rotating sleeve of up to 720°. A co-operating stop may be provided on the rotating sleeve, such as a stop element projecting out from the external face of the rotating sleeve, thereby producing a radial stop restriction, i.e. the rotating sleeve can be rotated only so far in the setting sleeve until the co-operating stop element of the rotating sleeve lies against the stop of the setting sleeve, thereby preventing the rotating sleeve from being rotated further relative to the setting sleeve. Thus, the injection device is primed prior to dispensing a dose as far as a position fixed by a rotation position of the setting sleeve. The stop element of the rotating sleeve may restrict the maximum setting rotation of the setting sleeve to approximately 360°, 720° or other suitable rotational amount. An axial or spiral or screw-shaped stop element may also be provided on the rotating sleeve which co-operates with one or more co-operating stop elements of the setting sleeve.

The marking or markings on the setting sleeve may extend circumferentially, i.e. without an axial offset, or may alternate with a changing axial offset for example, so that the markings 0.2, 0.4, 0.6 . . . are disposed extending radially around the setting sleeve and the markings 0.1, 0.3, 0.5 . . . lying in between may be disposed axially offset from them. The markings on the rotating sleeve may be provided in exactly the same way as on the setting sleeve or may be stepped or staggered, i.e. markings indicating a higher value, e.g. adjacent to the offset in the circumferential direction, may also be offset in the distal or proximal direction for example, so that when the rotating sleeve is rotated out of the setting sleeve, the marking value associated with the respective set or primed quantity is always fully legible once the setting sleeve has been rotated out far enough so that the dose assigned to this marking can be dispensed when the rotating sleeve is pushed in or rotated in or slid in. It is therefore not yet possible to take a full reading of markings associated with a higher value.

Using the markings provided on the rotating sleeve, a reading can be taken as to whether a dose set by the setting sleeve has been correctly primed or, if the dose setting mechanism contains a restriction mechanism such as a locking element for example, as will be described below, whether the dose set by the setting sleeve is still contained in the injection device or an ampoule contained in it and can be dispensed, so that a user can ascertain that a dose set in readiness for administering can not yet or can no longer be dispensed from the injection device.

The invention further relates to a method of preparing to dispense a dose of substance to be dispensed from an injection device, whereby the quantity of the dose to be dispensed can be set by a setting element, in particular a setting sleeve, by rotating the setting element, and a priming element is provided, e.g., a rotating sleeve, so that the process of dispensing the substance is performed by rotating the priming element out, and once the dose has been set, because of a mechanical coupling between the setting element and priming element, the priming element can only be rotated out as far as a restriction, to a point at the restriction where a marking provided on the priming element defining a dose is disposed in the axial extension of an associated set dose marking on the setting element. The present invention further relates to a method of preparing to dispense a dose of substance to be dispensed from an injection device wherein, using a setting element, e.g. a setting sleeve, the quantity of dose to be dispensed is set by rotating the setting element, and by a priming element, e.g. a rotating sleeve, the substance is prepared for dispensing by rotating the priming element out, and a lock element moved in the direction towards an end position, e.g. an end stop, with every priming operation restricting the outward rotating movement of the priming element if the available quantity of substance to be dispensed is smaller than the quantity of the dose to be dispensed which was set with the setting element.

By virtue of another aspect, the present invention relates to a dose setting mechanism for setting a dose to be dispensed form an injection device, the dose setting mechanism comprising a setting sleeve which can be pushed relative to the dose setting mechanism or relative to an injection device connected to or coupled with it, e.g. rotated or turned and moved axially, to set a quantity or dose of a substance to be dispensed from the injection device. A rotating sleeve is coupled with the setting sleeve and can be rotated, turned or screwed out of the dose setting mechanism or injection device to prepare for dispensing a dose so that the injection device can be primed, i.e. a substance that will be dispensed when the rotating sleeve is rotated back or pushed back into the dose setting mechanism or injection device is prepared in readiness for dispensing.

In accordance with some embodiments of the present invention, a rotation restricting element is provided on the setting sleeve or is coupled with it, such as a radial stop in the form of a web or strip extending in the axial direction or in a spiral, the rotational position of which relative to the injection device can be varied by a setting or rotating movement of the setting sleeve. Provided on the rotating sleeve or coupled with the rotating sleeve is a co-operating stop, which ensures that the rotating sleeve can be rotated out of the setting sleeve or injection device only to the degree that the rotating movement of the rotating sleeve is restricted by the stop of the setting sleeve moving into contact with the co-operating stop of the rotating sleeve. Accordingly, depending on the design of the stop and co-operating stop elements, a maximum rotation angle can be fixed for the rotating sleeve to prepare for dispensing a substance, which, for example if using an axially extending external element permitting a full rotation, might be 360°, or 720° if using a stop element which permits two rotations. In some embodiments, the process of setting a dose by the setting sleeve is independent of an outward rotating movement of the rotating sleeve, i.e. once a dose has been fixed by the setting sleeve, it can be dispensed repeatedly from the injection device without performing another setting operation if the rotating sleeve is always rotated out as far as the stop and then rotated or pushed back in again to dispense the substance. In some embodiments, the process of setting a dose is therefore uncoupled from the process of priming the injection device and may be undertaken by a doctor, who can lock the setting sleeve in the setting position relative to the injection device by an optionally provided locking element, so that it is no longer possible for a user to dispense too high a dose from the injection device. By rotating the rotating sleeve out as far as a radial stop position pre-set by the setting sleeve, a user will always be able to prime the injection device correctly. Consequently, a "dose memory" can be set up or established without the need for any coupling movement to couple and uncouple the setting sleeve and rotating sleeve.

In some embodiments, the stop may be provided in the form of a radial stop on the internal face of the setting sleeve, e.g. in the form of a web extending in the axial direction or alternatively in a spiral shape around the internal face, the rotational position of which can be varied by a rotation of the setting sleeve relative to the injection device. The co-operating stop may be provided in the form of a web or cam projecting radially out from the rotating sleeve, which projects sufficiently from the external face of the rotating sleeve that when the projecting cam is rotated and/or guided in a thread of the injection device, it lies against the stop of the setting sleeve after a predefined rotation angle and therefore prevents any further rotation of the rotating sleeve.

As mentioned above, the setting sleeve may have a locking or fixing element, by which the setting position of the setting sleeve can be fixed or locked relative to the injection device. Another option is one whereby the setting sleeve can be turned relative only to the injection device or a housing thereof when the rotating sleeve is in a predefined positional relationship with respect to it, e.g. fully pushed in. To this end, a circumferentially extending cut-out, groove or recess may be provided on the rotating sleeve but if the rotating sleeve is not in the fully pushed-in state it will not lie opposite one or more catch cams of the setting sleeve which engage in catch orifices provided on the internal face of an injection housing or some other element and thus prevent the setting sleeve from turning relative to the injection device or housing of the injection device. It is not until a circumferentially extending groove of a rotating sleeve guided in the setting sleeve lies opposite the catch elements of the rotating sleeve that the latter can be released and moved out of the engagement locking the rotation position of the setting sleeve, so that the setting sleeve can be turned to set a dose. When the rotating sleeve is rotated out of the setting sleeve, for example, in other words offset from it in the axial direction, the circumferentially extending groove of the rotating sleeve no longer lies opposite the catch elements of the setting sleeve so that they engage in corresponding co-operating catch elements or engagements of the injection device and prevent the setting sleeve from being turned relative to the injection device or a housing thereof.

By virtue of another aspect, the present invention relates to a dose setting mechanism for setting a dose to be dispensed from an injection device, with a setting sleeve for setting the dose, e.g. by turning the setting sleeve relative to the injection device, which setting sleeve does not change relative to the injection device, in other words is not extracted from it or pushed into it. For the purpose of the present invention, a rotating sleeve is provided and co-operates with or is coupled to the setting sleeve in such a way that it is not extracted proximally when setting a dose but, independently of the setting operation, can be rotated out of the injection device out from the housing after the dose setting operation to prime the injection device. This ensures that the setting operation can be uncoupled from the operation of priming the injection device or is independent of it, which means that there is no possibility of an incorrect dose or overdose when priming the injection device.

The present invention further relates to a method of setting a dose to be dispensed from an injection device, whereby the dose to be dispensed can be set by a setting element, e.g. a setting sleeve, after which the injection device can be primed by a priming element, e.g. a rotating sleeve, so that the set dose can then be dispensed from the injection device in a subsequent step, in which case the setting operation is uncoupled or independent from the priming operation.

By virtue of another aspect, the present invention relates to a dose setting mechanism for setting a dose to be dispensed from an injection device, with a rotating sleeve which can be rotated out of the injection device to prime the injection device and which has an internal thread. A threaded rod is guided in the rotating sleeve and can be moved relative to the rotating sleeve. A lock element provided on the threaded rod and having an external thread able to engage in the internal thread of the rotating sleeve is mounted so that it can slide but is prevented from rotating and can be screwed or turned forwardly as far as a front or distal stop element of the rotating sleeve thereby causing a restriction to the priming movement of the rotating sleeve in the fully forward state. If the threaded rod is mounted in the injection device by a first anti-rotation or back-rotation lock so that it is prevented from turning during a priming operation, when the rotating sleeve is rotated out of the injection device, the thread pitches, if the external thread of the lock element engaging in the internal thread of the rotating sleeve runs or extends in the same direction as the external thread of the rotating sleeve screwed into the injection device, the lock element is screwed relative to the rotating sleeve in the distal direction during a rotating movement of the rotating sleeve out of the injection device in the proximal direction. When the rotating sleeve is turned back into the injection device, the relative position between the lock element and rotating sleeve remains unchanged when the threaded rod rotates in conjunction with the rotating sleeve, which may be made possible by providing a second anti-rotation lock or back-rotation lock on the rotating sleeve or connected to it. Due to the distal screwing action of the lock element into the rotating sleeve during a priming operation of the rotating sleeve, it is possible to ascertain the total quantity of a substance which can be dispensed from the injection device by the dose setting mechanism before the lock element has been fully screwed into the rotating sleeve, or has reached a stop position preventing the rotating sleeve from being pulled out further if the rotating sleeve is mounted on the threaded rod so that it can not rotate and is held in the injection device by a first anti-rotation lock so that it is not able to rotate during the priming operation. This being the case, the lock element is able to block the rotating sleeve at the last dose setting and thus block settings higher than the available quantity of substance to be dispensed.

If the initial or starting position of the lock element on the threaded rod or in the rotating sleeve is fixed so that the priming operations needed to rotate the lock element distally inwardly as far as a stop is not greater than the associated quantity of substance contained in the injection device or corresponds to it, this will ensure that it is impossible to prime a dose which can no longer be dispensed from the injection device. This prevents incorrect doses when dispensing the last dose from the injection device, and a user will be able to determine from the maximum last priming position blocked by the lock element what quantity of substance can still be dispensed from the injection device, so that the user will no longer use the injection device or will dispense the remaining quantity of substance from the injection device and make up the missing extra quantity for a treatment from another injection device or another ampoule.

In some preferred embodiments, the thread of the threaded rod and the external thread of the lock element run or extend in the same direction.

In accordance with the present invention, an anti-rotation lock or back-rotation lock or stop designed to enable the threaded rod to be turned in one direction relative to the injection device or relative to the rotating sleeve and block or prevent a rotation in the opposite direction will be explained below. The rotation locks on the injection device and the rotating sleeve may be of the same or similar construction and operate on the basis of the same or similar mechanism, e.g. as the type of construction, operation or mechanism known as a ratchet system.

In some embodiments, the present invention further relates to a method of restricting a maximum possible dose or setting quantity of an injection device, wherein during a priming operation of the injection device prior to dispensing the dose to be dispensed from the injection device, a lock element is moved in the direction toward a stop, locking or blocking position and, depending on the distance of the lock element from the locking or blocking position, the maximum quantity of substance to be primed with a dose setting mechanism or dispensed from the injection device is set.

By virtue of another aspect, the present invention relates to a threaded rod which is capable of exerting a pressure on a stopper in a reservoir of an injection device containing a substance to be dispensed, as well as to a dose setting mechanism for setting a dose or substance to be dispensed from an injection device incorporating such a threaded rod.

In some embodiments, the injection device has a rotating sleeve, by which a dose to be dispensed from the injection device can be primed or set by rotating the rotating sleeve, in other words by screwing or turning the rotating sleeve out of or into the injection device. On its external face, the threaded rod has a thread, which may be provided in the form of a circumferentially extending thread or may comprise several thread part-portions offset axially and/or in the circumferential direction, and is guided in the injection device and/or the setting sleeve and is axially displaceable therein by a rotation restricting element provided on the internal face of the injection device or setting sleeve. The thread of the threaded rod may be provided in the form of a web projecting from it or in the form of a groove recessed into it.

In some embodiments, a rotation restricting element is provided on the injection device and/or the setting sleeve and/or the rotating sleeve. The restricting element may be fixedly connected to the housing of the injection device for example, and may be provided in the form of a rotation locking ratchet, an anti-rotation lock or a back-rotation lock. A rotation restricting element within the meaning of the present invention is an element which, in co-operation with an element guided by or in the rotation restricting element, such as the threaded rod, permits a rotation of the guided element, such as the threaded rod, in one direction only and blocks or prevents a rotation in the opposite direction. To this end, appropriate co-operating elements may be provided on the threaded rod. For example, it is possible to use a combination of catch lugs or cams on the rotation restricting element or threaded rod which engage in co-operating catch points such as a ratchet or teeth of the threaded rod or rotation restricting element, which operate on the principle of known ratchet systems. A catch lug may be provided on an elastic element biased in the radial direction, such as a catch arm, which is disposed in the circumferential direction of the guided element, on it or on the rotation restricting element, or which may be disposed directly on the respective element without an elastic element and which has an oblique surface on one side to enable it to slide out of a catch point. The side opposite the oblique surface is not oblique and prevents a rotation of the catch element in the opposite direction which would be necessary for it to slide out.

In some embodiments, the thread provided on the threaded rod may have toothing or teeth on the thread or thread segment in which one or more catch elements or one or more rotation restricting elements can engage to permit a rotation of the threaded rod relative to the rotation restricting element in one direction only. A threaded rod may therefore only be screwed into or out of a setting sleeve connected to a rotation restricting element, in which case the respective opposite rotating movement is blocked by the rotation restricting element.

In some preferred embodiments, like the rotating sleeve, the injection device also has a rotation restricting element which permits a rotation of a threaded rod in the same direction and blocks it in the opposite direction. Since the rotating sleeve is mounted in the injection device so that it can rotate and is guided by a thread, and because it can be pulled and/or screwed out of it to prime the injection device and can be pushed and/or screwed in to dispense a dose, a back-rotation lock provided on the rotating sleeve enables the threaded rod to be retained by the anti-rotation lock of the injection device as the rotating sleeve is being rotated out of the injection device, while the rotation lock of the rotating sleeve permits an outward rotating movement out of the injection device. When the rotating sleeve is screwed back into the injection device, the rotation restricting element of the rotating sleeve engages in the threaded rod and causes the rotating sleeve to transmit the turning movement into the injection device to the threaded rod, driving the latter with it, thereby enabling the threaded rod to rotate as well due to the rotation restriction element of the injection device, which blocks rotation of the threaded rod during the process of screwing the rotating sleeve out of the injection device.

Since, in some embodiments, the threaded rod also rotates as the rotating sleeve is being rotated in, the threaded rod can be pushed distally in the injection device, guided in a thread of the injection device to push a stopper by a defined distance into a container, such as an ampoule, thereby causing a fluid or substance contained in the container to be forced out and thus administered to a patient through a dispensing orifice of the container.

In some embodiments, a rotating knob may be mounted on the rotating sleeve, which can be turned relative to the rotating sleeve, thereby enabling a user to pull or rotate the rotating sleeve out of the injection device by pulling on the rotating knob without the rotating knob being turned relative to the injection device, in which case the rotating sleeve is rotatably retained in the rotating knob. The rotating sleeve can also be pushed into or rotated or screwed into the injection device by applying pressure to the rotating knob without the rotating knob moving relative to the injection device.

BRIEF DESCRIPTION OF THE DRAWINGS

FIGS. 2A-2H illustrate the positions of one embodiment of a dose setting mechanism when setting a dose, priming an injection device and dispensing a dose;

FIGS. 3A and 3B illustrate one embodiment of an anti-rotation lock in accordance with the present invention; and FIGS. 4A-4C illustrate another embodiment of an anti-rotation lock in accordance with the present invention.

DETAILED DESCRIPTION

Figure 1B:
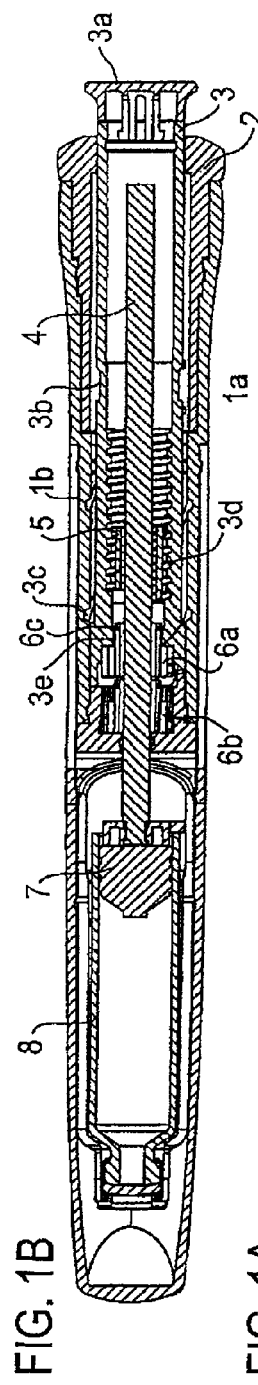
FIG. 1B is a sectional view along line B-B indicated in FIG. 1A.
Figure 1A:
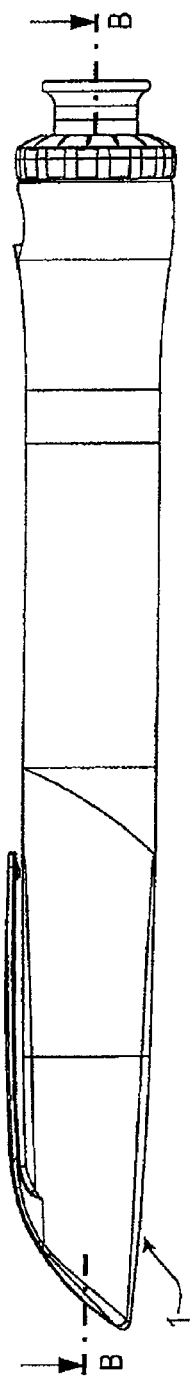
FIG. 1A is a side view of an embodiment of an injection device in accordance with the present invention.
Figure 1D:
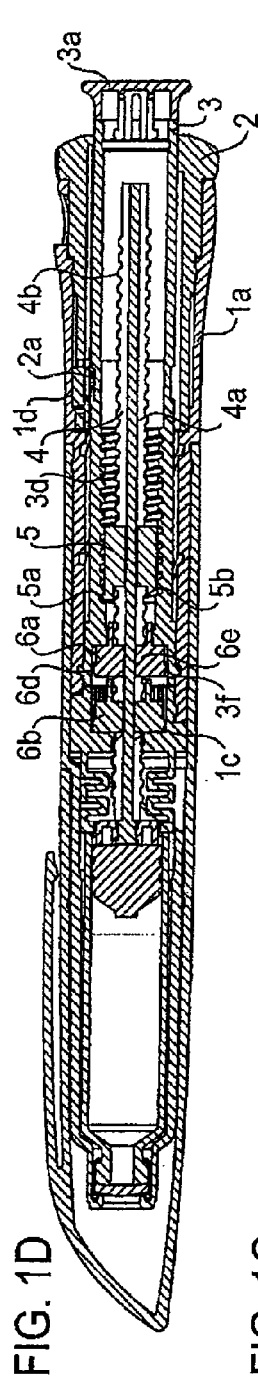
FIG. 1D is a sectional view along line D-D indicated in FIG. 1C.
Figure 1C:
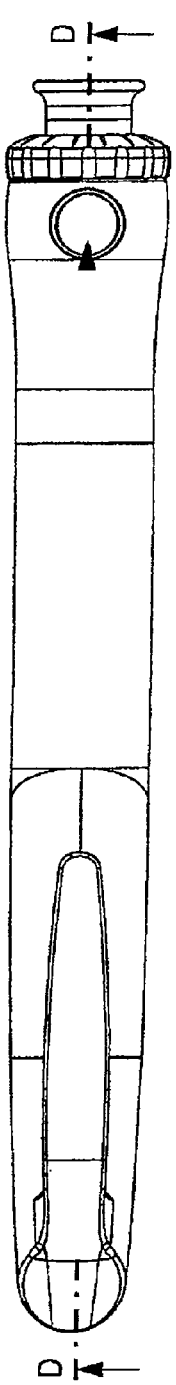
FIG. 1C is a plan view of the injection device illustrated in FIG. 1A.

FIG. 1A shows a side view of an embodiment of an injection device (1) in accordance with the present invention, a section of which through line B-B is illustrated in FIG. 1B.

The injection device (1) has a housing or housing element (1a), in which a setting sleeve (2) is disposed so that it can be rotated for initially pre-setting a dose or setting the injection device, e.g. by a doctor, or alternatively for setting different dose quantities several times. Mounted so as to rotate inside the setting sleeve (2) is a rotating sleeve (3) with an external thread (3c) which engages in an internal thread (1b) of the injection device (1) or a housing part (1a) of the injection device. The rotating sleeve (3) has an internal thread (3d), which engages in an external thread (5a) of a lock element (5) so that the rotating sleeve (3) sits in threaded engagement with the injection device (1) or a housing (1a) thereof and sits in the threaded engagement by virtue of the lock element (5). The lock element (5) is mounted so that it is prevented from turning but is able to move axially on a threaded rod (4) and has two oppositely lying guide elements (5b) which engage in the axial direction in a guide groove (4a) extending along the threaded rod (4) so that a rotation of the threaded rod (4) is always transmitted to the lock element (5) which rotates with the threaded rod (4) and which can also block a rotation of the threaded rod (4) when it is fully screwed into the rotating sleeve (3).

Provided on the distal end of the rotating sleeve (3) is a rotation restricting element (6a), which is connected to the rotating sleeve (3) so that the rotation restricting element (6a) can not be released from the rotating sleeve (3) in the axial direction, and the rotation restricting element (6a) is retained by snappers or retaining elements (6c) of a driver (3e) of the rotating sleeve (3) so that, although the rotation restricting element (6a) is able to rotate relative to the rotating sleeve (3), it can not be pushed in the axial direction relative to the rotating sleeve (3).

The rotation restricting element (6a) has catch elements (6d) biased radially outwardly by resilient arms which engage in circumferentially extending teeth or a ratchet system (3f) provided on the internal face of the distal end of the rotating sleeve (3). The toothing (3f) and catch elements (6d) are designed so that the rotation restricting element (6a) is able to rotate in the rotating sleeve (3) in only one direction, in which the catch elements (6d) are able to slide out of engagement with the teeth (3f), whereas a rotation in the opposite direction is prevented by an appropriate design of the catch elements (6d) engaging in the teeth (3f), blocking an opposite direction movement so that the one-sided effect of the rotation restriction is used to provide a ratchet system generally similar to known types.

Like the lock element (5), the rotation restricting element (6a) also has mutually opposite guide elements (6e), which engage in the axial guide or groove (4a) of the threaded rod (4) and are thus prevented from rotating relative to the threaded rod (4), although the threaded rod (4) can be pushed axially relative to the rotation restricting element (6a).

Another rotation restricting element (6b) substantially identical in construction to the rotation restricting element (6a) is mounted so that it can rotate in the injection device (1) and engages with catch elements (6d) in teeth (1c) extending around the internal face of an injection device part so that the rotation restricting element (6a) can not be moved in the axial direction in the injection device (1) and is able to rotate in only one direction of the injection device (1) but is locked in the opposite direction.

Figure 2D:
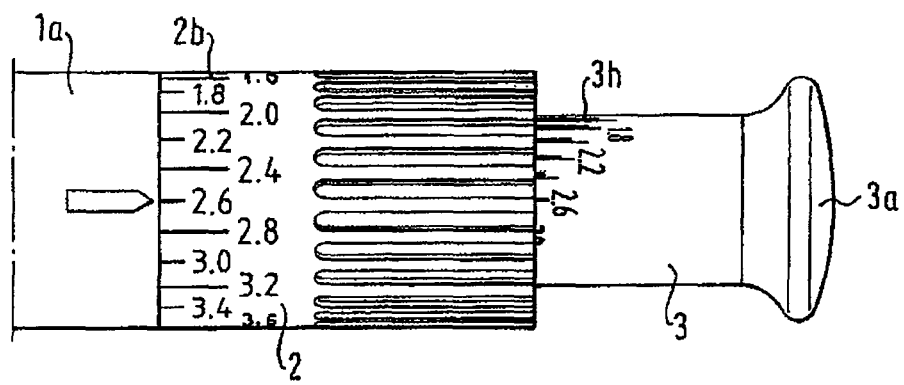

The mode of operation of an embodiment of an injection device in accordance with the present invention will be described with reference to the states of an embodiment of a dose setting mechanism in accordance with the present invention as illustrated in FIGS. 2A-2H. FIG. 2A is a plan view and cross-sectional view of a dose setting mechanism with a threaded rod (4), which is flattened and has an approximately rectangular cross-section in the embodiment illustrated, having thread segments 4b on two oppositely lying side faces, between which lie part-pieces of the threaded rod (4) which are not provided with thread elements. The threaded rod (4) is mounted in the lock element (5) or the rotation restricting elements (6a, 6d) so that it can not rotate due to the fact that end-to-end orifices more or less matching the cross-sectional shape of the threaded rod (4) are provided in these elements.

By turning on the rotating sleeve (3), a desired dose to be primed and dispensed is set. The setting lock cam (2a) of the setting sleeve (2) is released towards the interior and can be pushed into the release groove (3b) to release the coupling of the setting sleeve (2) with the housing (1a) by engaging the setting lock cam (2a) in catches lying on the internal face of the housing (1a).

Once the dose has been set by the freely rotatable setting sleeve (2), the injection device is primed, as illustrated by the plan view and cross-sectional view in FIG. 2B. By pulling on the freely rotatable rotating knob (3a), the injection device is primed or charged with the dose of 2.6 units, for example, previously set by the setting sleeve (2). The rotating sleeve (3) is pulled together with the freely rotatable rotating knob (3a) in the proximal direction (to the right in FIG. 2B) and turns due to the thread engagement of the external thread (3c) of the rotating sleeve (3) in the internal thread (1b) of the injection device housing (1a).

A stop bar (2b) provided on the internal face of the setting sleeve (2), the radial position of which was fixed by the setting or rotating operation of the setting sleeve (2), limits a maximum possible rotating or priming movement of the rotating sleeve (3), which has a stop element (3g) on its external face, in the form of a projecting cam for example. As illustrated in FIG. 2C, the rotating sleeve (3) can be rotated out of the injection device (1) until the stop element (3g) lies against the stop bar (2b) of the setting sleeve and thus prevents any further rotation or extraction of the setting sleeve (2).

As may be seen from FIGS. 2B and 2C, the release groove (3b) provided on the rotating sleeve (3) is moved away from the setting lock cam (2a) of the setting sleeve (2) during a priming operation when the rotating sleeve (3) is being extracted, so that the setting lock cam (2a) is no longer able to flex radially inwardly and thus engages or locks in the ratchet system (1d) provided on the internal face of the housing (1a) due to an engagement, thereby preventing a radial or rotating movement of the setting sleeve (2) relative to the injection device (1) or housing element (1a). A dose set by the setting sleeve (2) can therefore no longer be changed during a priming and dispensing operation when the rotating sleeve (3) is at least partially extracted.

During a priming operation, the lock element (5) in the interior of the setting sleeve (2) rotates into and relative to the setting sleeve (2), i.e. the lock element is moved relative to the setting sleeve (2) in the distal direction of the setting sleeve (2), because the lock element is mounted on the threaded rod (4) so that it can not rotate and the rotating sleeve (3) is rotated relative to the lock element (5) as it is rotated out, and the thread engagement of the lock element (5) in the internal thread (3d) of the rotating sleeve (3) ensures a relative movement of the lock element (5) in the axial direction of the rotating sleeve (3) during the outward rotating movement.

During the operation of priming the injection device, i.e. when the rotating sleeve (3) is being rotated out, the front rotation restricting element (6b) connected to the injection device prevents the threaded rod (4) from turning as well, while the injection device is being primed, whereas the rotation restricting element (6a) connected to the rotating sleeve (3) permits a rotating movement of the rotating sleeve (3) relative to the threaded rod (4) retained by the rotation restricting element (6b).

As illustrated in FIG. 2D, in some embodiments, a marking is provided on the external face of the setting sleeve (2) in the circumferential direction, and in the case of the setting shown in FIG. 2D, a dose of 2.6 has been set by turning the setting sleeve (2) so that a rotation position marked by a dash associated with the dose 2.6 lies against a marking element on the housing (1a) indicated by an arrow. When the rotating sleeve (3) is in the fully extracted state defined by the stop of the stop element (3g) on the stop bar (2b), the rotating sleeve (3) has been rotated so far out of the injection device that a marking of the actually primed dose 2.6 provided on the circumferential face of the rotating sleeve (3) is fully visible, and the marking 2.6 on the rotating sleeve (3) lies in the axial extension of the marking 2.6 of the setting sleeve (2), indicating to a user that the set dose has actually been primed. A user can also compare the set dose with the primed dose by looking at the injection device, without having to compare a set dose indicated on one side of the injection device with an "actually primed" dose displayed on a different side of the injection device.

Figure 2G:
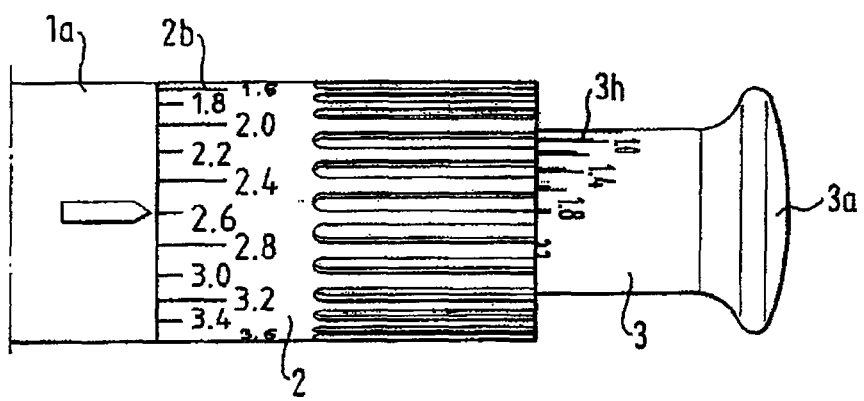
Figure 2E:
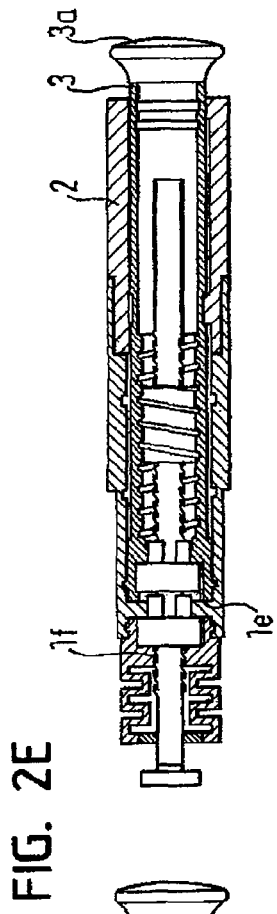
Figure 2E:

The rotating knob (3a) can be pushed to dispense a pre-set dose, causing the rotating sleeve (3) rotatably mounted in the rotating knob (3a) to be rotated into the injection device, as illustrated in FIG. 2E, until a front or distal end of the setting sleeve (2) lies against an internal stop (1e) of the injection device (1). When the setting sleeve (2) is rotated in, the front rotation restricting element (6b) connected to the injection device (1) releases the rotating movement of the threaded rod (4), which is retained by the rotation restricting element (6a) connected to the rotating sleeve (3) and is rotated together with the rotating sleeve (3) relative to the injection device (1) and is thus screwed in the distal (forward) direction due to a thread engagement in an internal thread (1f) of the injection device (1) relative to the injection device (1) to push a stopper (7) lying against the front face of the threaded rod (4) into an ampoule (8), as illustrated in FIG. 1B, and force a substance contained in the ampoule (8) out, thereby enabling a pre-set dose to be dispensed.

Once the dispensing operation has been completed, the dose set by the rotating sleeve (3) can be primed again by simply extracting the rotating sleeve (3) and then dispensed in the manner described above, without having to set a dose again, because the setting or rotation position of the setting sleeve (2) was not changed during the priming and dispensing operation.

If the lock element (5) is inserted in the rotating sleeve (3) so that the total possible distance to be traveled by the lock element (5) until it reaches a front stop inside the rotating sleeve (3) corresponds to a desired maximum quantity of substance to be dispensed, the priming operation of the injection device can be restricted by blocking the outward rotation of the rotating sleeve (3) if a dose set by the setting sleeve (2) is greater than the predefined maximum permissible total dispensing quantity.

Figure 2F:
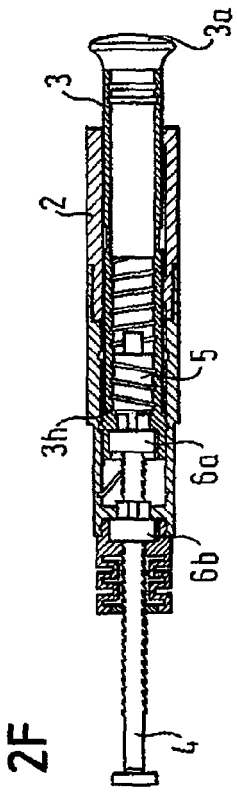
Figure 2F:

If a last permissible dose is primed, for example as illustrated in FIG. 2F, the rotating sleeve (3) is again extracted or rotated out from the injection device (1) by the rotating knob (3a). At the same time, the lock element (5) in the interior of the rotating sleeve (3) is rotated into the rotating sleeve (3) until the lock element (5) lies against a front stop (3h) of the rotating sleeve (3) and thus prevents any further outward rotation of the rotating sleeve (3), which is retained by the thread engagement with the external thread (5a) of the lock element (5), which is not able to rotate relative to the injection device because it is mounted so that it can not rotate on the threaded rod (4), which is retained so that it can not rotate by the front rotation restricting element (6b) connected to the injection device (1) during the extraction or priming operation.

As illustrated in FIG. 2G, a user can easily see that the maximum dose of 1.8 which can still be primed is displayed in the axial extension of the marking 2.6 provided on the setting sleeve (2) when the rotating sleeve (3) is in the blocked, extracted end state, in which case a user will easily be able to tell that the desired set dose can no longer be dispensed.

Figure 2H:
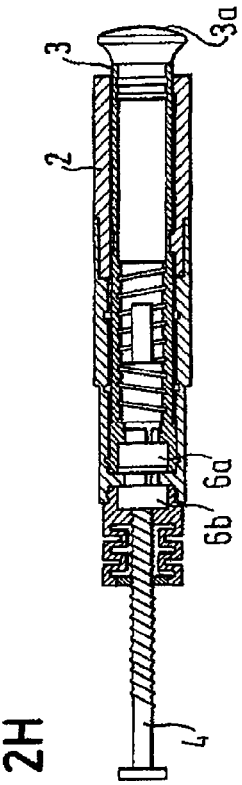
Figure 2H:

As illustrated in FIG. 2H, the last dose can be dispensed by depressing the rotating knob (3a). The fact that the lock element (5) is fully screwed into the rotating sleeve (3) and sits against the front stop (3h) of the rotating sleeve (3) makes it impossible to prime the injection device again.

Due to the difference in the thread pitches of the external thread (4b) of the threaded rod (4) and the external thread (3c) of the rotating sleeve (3), a reduction in the ratio of the dispensing operation can be achieved, for example, if the thread pitch of the external thread (3c) of the rotating sleeve (3) is greater than the external thread (4b) of the threaded rod (4). During priming, the rotating sleeve (3) is extracted farther out of the injection device (1) than the threaded rod (4) is pushed axially in the distal direction as the rotating sleeve (3) is pushed in because during the pushing-in or dispensing process, the rotating sleeve (3) is coupled in rotation with the threaded rod (4) and the two elements therefore effect the same rotating movement. Since the external thread (3c) of the rotating sleeve (3) has a greater pitch than the external thread (4b) of the threaded rod (4), a larger priming and pushing-in movement of the rotating sleeve (3) in an axial direction will cause a shorter forward movement of the threaded rod (4), which leads to a finer dose setting of the substance dispensed out of an ampoule (8) by a forward movement of the threaded rod (4). The ratio of the pitch of the external thread of the rotating sleeve (3) to that of the external thread of the threaded rod (4) may be set so that there is an increase in ratio, no increase in ratio, or a decrease in ratio.

Figure 3B:
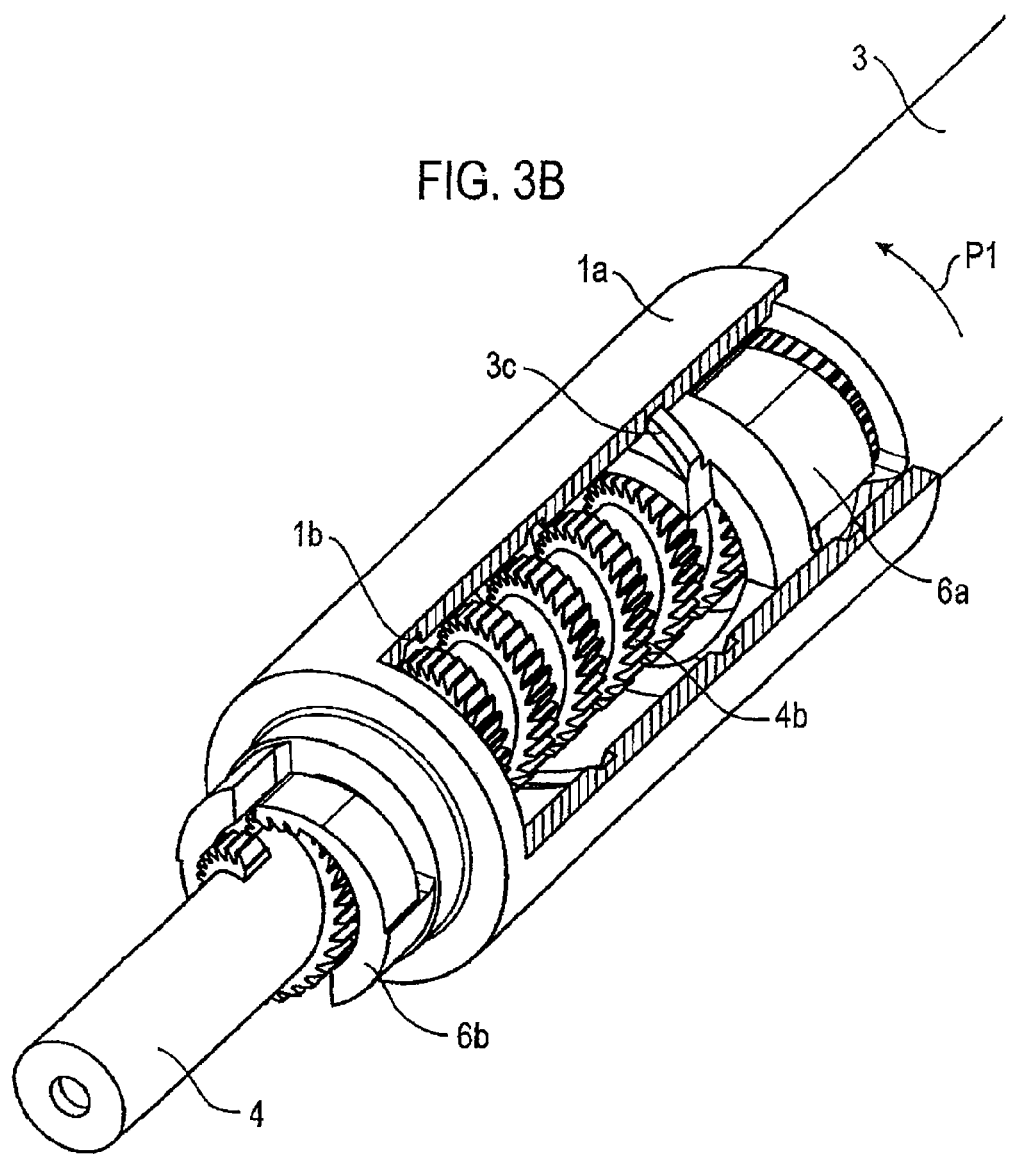

FIGS. 3A and 3B illustrate a different embodiment of the rotation restricting elements 6a and 6b. In the embodiment illustrated, the threaded rod (4) has a circumferentially extending thread (4b) with teeth in the circumferential direction, and the individual teeth are designed so that a catch or retaining action can be achieved with a co-operating set of teeth or a catch element on one tooth flank, while the other tooth flank is designed so that a sliding movement or displacement is possible on a catch or co-operating element. For example, the tooth flank causing an engagement or retaining action may extend essentially outwardly in the radial direction while the tooth flank permitting a rotating or sliding movement is oblique or inclined with respect to the other tooth flank.

Fixedly connected to or integrated in the injection device (1) or a housing part (1a) thereof is a rotation restricting element (6b) which has catch elements (6f) formed respectively by three tooth flanks in the embodiment illustrated, which lie opposite one another and are mounted on elastic or catch arms (6g). The thread (4b) is guided by an internal thread inside the injection device (1) or housing part (1a) so that the threaded rod (4) is mounted by a threaded engagement so that it can rotate in the injection device (1) or housing part (1a) and can be screwed into and out of it. Due to the engagement of the catch elements (6f) in the teeth provided on the thread (4b) of the threaded rod (4), the threaded rod (4) can be rotated relative to the housing part (1a) in one direction only, whilet a movement in the opposite direction is blocked. In the embodiment illustrated in FIG. 3A, the threaded rod (4) can be rotated in the clockwise direction, whereas the threaded rod (4) can only be screwed out of the housing part (1a) in the distal direction but can not be turned in the opposite direction.

The rotation restricting element (6a) fixedly connected to the rotating sleeve (3) or integrated with it is of the same or similar construction as the rotation restricting element (6b), also has catch elements (6f) mounted on elastic arms (6g) extending round the threaded rod (4) and can engage in the teeth of the thread (4b) of the threaded rod (4) to permit a rotating movement between the threaded rod (4) and rotating sleeve (3) in one direction and block it in the opposite direction, as described above.

FIG. 3A illustrates the rotating sleeve (3) fully rotated into the injection device and guided by an external thread (3c) in an internal thread (1b) of the injection device housing (1a).

When the injection device (1) is being primed by rotating the rotating sleeve (3) out, the threaded rod (4) is retained by the rotation restricting element (6b) so that it is prevented from rotating relative to the injection device housing (1a), whereas the rotation restricting element (6a) is not in a blocking engagement with the teeth on the thread (4b) of the threaded rod (4) in the direction of rotation indicated by arrow P1, which would cause the rotating sleeve (3) to be rotated out of the housing (1a).

When the rotating sleeve (3) is rotated back in the direction indicated by arrow P2 in FIG. 3A, the engagement elements of the rotation restricting element (6a) of the rotating sleeve (3) engage with the teeth of the thread (4a) of the threaded rod (4), as a result of which the threaded rod (4) is coupled with the rotating sleeve (3) so that it can not rotate as the rotating sleeve (3) is being rotated inwards and is picked up by the latter and rotated with it. The rotation restricting element (6b) of the injection device (1) permits a rotation of the threaded rod (4) relative to the injection device (1) or housing (1a) so that the threaded rod (4) is not rotated by the rotating sleeve (3), and is guided in the internal thread of the injection device (1) or housing (1a) and is thus rotated out of the housing (1a) in the distal direction to dispense a set and primed dose. The injection device can then be primed again by rotating the rotating sleeve (3) out in the direction indicated by arrow P1 FIG. 3B.

The embodiment of the rotation restricting elements 6a and 6b illustrated in FIGS. 3A and 3B may be used in a dose setting mechanism or injection device instead of the rotation restricting elements 6a and 6b described in connection with FIGS. 1 and 2, in which case all the other elements of the injection device may remain unchanged. For example, the lock element (5) may be guided on the threaded rod (4) to prevent it from rotating by providing one or more engaging elements in the axial direction on the internal face of the lock element (5), which can be guided in the teeth of the external thread (4b) of the threaded rod (4), thereby enabling the lock element (5) to be mounted on the threaded rod (4) so that it can move axially but is prevented from rotating.

FIGS. 4A-4C illustrate another embodiment of a rotation restricting element 6a or 6b, which may be disposed on a housing (1a) of the injection device or on the rotating sleeve (3) or integrated in these elements. The operating mechanism is the reverse of the embodiment described in connection with FIGS. 3A and 3B. Thread portion elements (4c) are provided on the threaded rod (4), which are attached to the threaded rod (4) by elastic support arms (4d) biased radially outwards, for example, and can engage in an internal teeth (1j or 3j) of the injection device housing (1a) or the rotating sleeve (3). Provided on the internal face of the housing (1a) or rotating sleeve (3), axially offset from the ratchet system or teeth 1j, 3j, is a thread or thread portion (1k, 3k), in which the external thread of the threaded rod (4) formed by the catch elements (4c) and support arms (4d) can be guided.

The threaded rod (4) can therefore be rotated into the housing (1a) or into the rotating sleeve (3), in which case the catch elements (4c) of the threaded rod co-operating with the ratchet system (1j, 3j) allow the threaded rod (4) to rotate relative to the housing (1a) or relative to the rotating sleeve (3) in a predefined direction only and block it in the opposite direction, as explained with respect to the embodiment illustrated in FIGS. 3A and 3B.

Like the rotation restricting element 6a or 6b illustrated in FIGS. 3A and 3B, the embodiment illustrated in FIGS. 4A-4C can also be used in conjunction with the injection device or dose setting mechanism illustrated in FIGS. 1 and 2 instead of the rotation restricting elements 6a and 6b specifically described in conjunction with them.

The lock element (5) may be mounted on the threaded rod (4) so that it can not rotate, for example by providing a guide recess or groove on the internal face of the lock element (5) in which engagement or catch elements (4c) can engage.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A dose setting mechanism for setting a dose to be dispensed from an injection device, comprising:
   an injection device housing;
   a setting element axially fixed and rotatably coupled to the housing; and
   a priming element rotatably mounted in the setting element;
   wherein the setting element rotates relative to the housing and the priming element in a dose setting movement to set the dose and an axial position of the setting element and the priming element relative to the injection device housing is maintained;
   wherein the priming element comprises an external threading forming a threaded engagement with an internal threading of the injection device housing, and the priming element turns out of the dose setting mechanism by a rotating and axial movement along the threaded engagement to draw up the set dose;
   wherein the setting element and priming element each comprises a stop, the stops co-operating upon drawing up the set dose so that the rotating movement of the priming element is relative to the setting element and is restricted by the stops;
   wherein the setting element comprises a setting lock cam and the priming element comprises a release groove, which aligns with the setting lock cam and the setting lock cam flexes radially inwardly to allow the dose setting movement of the setting element, and wherein when the priming element draws up the set dose, the release groove moves out of alignment with the setting lock cam and prevents the setting movement due to the setting lock cam being prevented from flexing radially inwardly.

2. The dose setting mechanism according to claim 1, wherein the setting element comprises a setting sleeve and the priming element comprises a rotating sleeve.

3. The dose setting mechanism according to claim 2, wherein the priming element travels an axial priming path having a length, and wherein the dose to be dispensed is proportional to the axial priming path length.

4. The dose setting mechanism according to claim 3, wherein the setting element and the priming element are disposed coaxially and can be turned relative to one another.

5. A dose setting mechanism for setting a dose to be dispensed from an injection device, comprising:
   a setting element comprising a setting sleeve axially fixed to an injection device housing, and
   a priming element comprising a rotating sleeve which screws out of the dose setting mechanism to draw up the set dose, the setting element and priming element rotatably disposed in the injection device housing,
   wherein the setting sleeve rotates relative to the injection device housing and the priming sleeve in a dose setting movement to set the dose and an axial position of the setting sleeve and the priming sleeve relative to the injection device housing is maintained,
   wherein a threaded engagement between the housing and the rotating sleeve rotatably couples the housing to the rotating sleeve and a stop is provided on the setting element and a co-operating stop is provided on the priming element so that rotating and axial movement of the priming element along the threaded engagement draws up the set dose and is restricted by the stops, and
   wherein the setting sleeve comprises a setting lock cam and the priming sleeve comprises a release groove, which aligns with the setting lock cam and the setting lock cam flexes radially inwardly to allow the dose setting movement, and wherein when the priming element draws up the set dose, the release groove moves out of alignment with the setting lock cam and prevents the dose setting movement of the setting sleeve due to the setting lock cam being prevented from flexing radially inwardly.

6. The dose setting mechanism as claimed in claim 5, wherein the dose to be dispensed from the injection device is dispensed by rotating the priming element along the threaded engagement.

7. The dose setting mechanism as claimed in claim 5, wherein the priming element travels an axial priming path having a selected length, the dose to be dispensed proportional to the selected axial priming path length.

8. The dose setting mechanism as claimed in claim 5, wherein at least one of the stop and co-operating stop is provided in the form of one of a web extending in an axial direction, a spiral shape or a projecting cam.

9. The dose setting mechanism as claimed in claim 7, wherein at least one of the stop and the co-operating stop is provided in the form of a projection extending at least partially in the circumferential direction around at least one of the setting element and the priming element, and the projection comprises a thread or a thread portion.

10. The dose setting mechanism as claimed in claim 5, wherein at least one of the stop and the co-operating stop is provided on one of an internal face or an external face of the setting element or the priming element.

11. The dose setting mechanism as claimed in claim 5, wherein the setting element and the priming element are disposed coaxially and can be turned relative to one another.

12. A dose setting mechanism for setting a dose to be dispensed from an injection device, comprising:
   a setting element comprising a setting sleeve; and
   a priming element comprising a rotating sleeve;
   wherein the dose to be dispensed is set by rotation of the setting element relative to the injection device and the priming element, wherein the setting element comprises a setting lock cam and the priming element comprises a release groove, and during rotation of the setting element, an axial position of the setting sleeve and the rotating sleeve relative to the injection device is maintained, the setting lock cam and the priming element align, and the setting lock cam flexes radially inwardly; and wherein the rotating sleeve rotates along a threaded engagement between the priming element and an injection device housing out of the dose setting mechanism to prepare for dispensing the set dose, and wherein as the rotating sleeve is rotated out of the dose setting mechanism to prepare for dispensing the set dose, the release groove moves out of alignment with the setting lock cam to radially bias the setting lock cam and prevent it from flexing radially inwardly such that the setting sleeve is locked against rotation, prevented from changing the set dose.

13. The dose setting mechanism as claimed in claim 12, wherein the movement of the setting element relative to the priming element is restricted by at least one of a stop and a co-operating stop.

14. The dose setting mechanism as claimed in claim 13, wherein the setting element locks relative to at least one of the injection device or relative the dose setting mechanism when the priming element is rotated.

15. An injection device comprising a dose setting mechanism comprising a setting element and a priming element, the setting element axially fixed to an injection device housing and rotates relative to the housing and the priming element to set a dose, and the priming element is turned out of the dose setting mechanism to draw up the set dose by a rotating movement of the priming element along a threaded engagement between the priming element and an injection device housing, the setting element and priming element each comprising a stop, the stops co-operating so that the rotating movement of the priming element is relative to the setting element and is restricted by the stops to define a maximum rotation angle of the priming element relative to the setting element and results in an axial translation of the priming element relative to the injection device corresponding to the set dose, wherein the setting element comprises a setting lock cam and the priming element comprises a release groove, and during rotation of the setting element to set the dose, an axial position of the setting element and the priming element relative to the injection device is maintained such that the setting lock cam and the priming element align and the setting lock cam flexes radially inwardly, wherein when the priming element is turned out of the dose setting mechanism, the release groove moves out of alignment with the setting lock cam to radially bias the setting lock cam and prevent it from flexing radially inwardly such that the setting element is locked against rotation relative to the injection device, which prevents changing the set dose.

16. The injection device according to claim 15, wherein the setting element comprises a setting sleeve and the priming element comprises a rotating sleeve.

17. The injection device according to claim 16, wherein the priming element travels an axial priming path having a length, and wherein the dose to be dispensed is proportional to the axial priming path length.

18. The injection device as claimed in claim 15, wherein the maximum rotation angle of the priming element relative to the setting element is approximately 360° or more.

19. A dose setting mechanism for setting a dose to be dispensed from an injection device, comprising:
a setting element comprising a setting sleeve for setting the dose to be dispensed;
a priming element for drawing up the set dose;
wherein the dose to be dispensed is set by rotation of the setting element relative to the injection device and the priming element, and an axial position of the setting sleeve and the priming element relative to the injection device and the priming element is maintained in a predefined positional relationship with the setting element during dosing such that a setting lock cam and a release groove of the dose setting mechanism are aligned and the setting lock cam flexes radially inwardly;
wherein the priming element comprises a rotating sleeve which rotates along a threaded engagement between the priming element and an injection device housing such that the rotating sleeve rotates out of the dose setting mechanism to draw up the set dose and the priming element moves out of the predefined positional relationship with the setting element and the setting lock cam is radially biased and prevented from flexing radially inwardly such that a rotational position of the setting sleeve relative to the injection device and the priming element is secured, and the rotational position of the setting sleeve can not be varied.

20. The dose setting mechanism as claimed in claim 19, wherein when the rotating sleeve is not rotated out of the dose setting mechanism, the release groove is configured as a circumferentially extending groove of the rotating sleeve and is provided opposite the setting lock cam configured as one or more catch cams of the setting sleeve such that the catch cams are released from an engagement with one or more catch orifices provided on an internal face of the injection device.

* * * * *